United States Patent

Kudo et al.

[11] 4,331,697
[45] May 25, 1982

[54] NOVEL HEPARIN DERIVATIVE, METHOD FOR PRODUCTION THEREOF, AND METHOD FOR RENDERING BIOMEDICAL MATERIALS ANTITHROMBOTIC BY USE OF THE NOVEL HEPARIN DERIVATIVE

[75] Inventors: Akira Kudo; Hiroo Inata; Makoto Ogasawara, all of Hino, Japan

[73] Assignee: Teijin Limited, Oraka, Japan

[21] Appl. No.: 183,377

[22] Filed: Sep. 2, 1980

[51] Int. Cl.$^3$ .............................................. A01N 1/02
[52] U.S. Cl. ...................................... 427/2; 424/183; 536/21
[58] Field of Search ............... 424/183; 536/21; 427/2

[56] References Cited

U.S. PATENT DOCUMENTS 3,211,617 10/1965 Bucourt .................................. 536/21
3,835,112 9/1974 Mardiquian ........................ 424/183
3,844,989 10/1974 Harumigs ............................ 424/183

FOREIGN PATENT DOCUMENTS 49-38945 4/1974 Japan ................................... 424/183

Primary Examiner—Sam Silverberg

[57] ABSTRACT

A heparin derivative in which at least 0.5% of the entire hydroxyl groups of heparin are in the form of an ester of the following formula

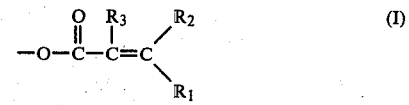

wherein $R_1$, $R_2$ and $R_3$ each represent a hydrogen atom or an alkyl group having 1 to 6 carbon atoms; a method for producing aforesaid heparin derivative which comprises reacting heparin with a halide or anhydride of an unsaturated carboxylic acid of the formula

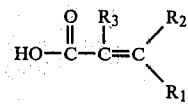

wherein $R_1$, $R_2$ and $R_3$ are the same as defined above; and a method for imparting antithrombotic activity to a biomedical material, which comprises treating that surface of the biomedical material which makes contact with the blood with actinic light in the presence of aforesaid heparin derivative.

5 Claims, 4 Drawing Figures

NOVEL HEPARIN DERIVATIVE, METHOD FOR PRODUCTION THEREOF, AND METHOD FOR RENDERING BIOMEDICAL MATERIALS ANTITHROMBOTIC BY USE OF THE NOVEL HEPARIN DERIVATIVE

This invention relates to a novel heparin derivative, a method for production thereof, and a method for imparting antithrombotic activity to that surface of a biomedical material which makes contact with the blood. More specifically, this invention pertains to a novel heparin derivative which is bound to a biomedical material through an active unsaturated group and imparts antithrombotic activity to the biomedical material, a method for producing said heparin derivative, and to a method for rendering a biomedical material antithrombotic.

In recent years, with a great advance in medical therapy, materials which make direct contact with the blood have been used on many occasions, for example in temporarily conducting the blood out of the body, or substituting artificial organs for organs within the body which make contact with the blood. Such materials include, for example, vascular catheters, cannulas, monitoring tubes, artificial kidneys, artificial heart-lungs, extracorporeal circuits for auxiliary circulating devices, A-V shunts, vascular prostheses, artificial heart valves, temporary blood by-path tubes, and film-like or hollow filament-like dialysis membranes.

Conventional materials (to be referred to as biomedical materials) which make direct contact with the blood are made from glass, metals, plastics such as soft vinyl chloride resins and silicone resins, and rubbers such as natural rubber. It is known that upon contact with such a biomedical material, the blood easily coagulates and forms a thrombus on its surface. The thrombus has a great danger of stopping the blood current or moves with the blood current to cause complications such as pulmonary thrombosis, cerebral thrombosis or myocardial infraction. In using these biomedical materials, therefore, it is the conventional practice to prevent thrombus formation by systemically administering an antithrombotic agent such as a preparation comprising heparin, coumarine, sodium citrate, etc. thereby to render the blood non-clotting. Systemic administration of heparin, etc., however, has the defect of causing a marked danger of bleeding.

If antithrombotic activity can be imparted to a biomedical material, it would be possible to prevent thrombus formation without systemically administering heparin, etc., and to safely perform medical treatment and diagnosis using these biomedical materials.

Some methods have been reported in the past about a method of imparting antithrombotic activity to a biomedical material by treating its surface with heparin known as an anticoagulant. One method comprises covalently binding heparin itself to the surface of a biomedical material to fix it there (see, for example, B. D. Halpern, et al., Interaction of Liquids at Solid Substrate, ed. R. F. Gould, Am. Chem. Soc., Pub. 1968; and A. S. Hoffman et al., TASAIO, 18, 10 1972). This method, however, was found to be ineffective, or effective only to a small extent. As a result, it was thought that heparin generally loses as antithrombotic activity or its antithrombotic activity decreases when it is covalently bound with another substance or compound.

There was suggested a method which comprises adhering or impregnating heparin to the surface or in the surface layer of a biomedical material, and releasing the heparin gradually into the blood during use [see, for example, R. I. Leininger, et al., Science, 152, 1625, 1966; A. Rembaum, et al., J. Macromol. Sci. Chem., A4 (3), 715, 1970; E. W. Merrill, et al. TASAIO, 12, 139, 1966]. According to this method, it is extremely difficult to control the release of heparin in such a manner that a moderate amount of heparin can be released over a long period of time. Hence, the antithrombotic activity lasts only for a short period of time, or an excessive amount of heparin is released to cause a danger of bleeding.

It is an object of this invention to provide a compound which can impart antithrombotic activity to a biomedical material while being covalently bound to it.

Another object of this invention is to provide a method for rendering the surface of a biomedical material antithrombotic over a long period of time, which comprises treating said surface with a compound capable of exhibiting antithrombotic activity while being covalently bound to that surface of the biomedical material which comes into contact with the blood.

The present inventors made extensive investigations in order to achieve the above objects, and found that these objects of the invention can be achieved by using an ester derivative of heparin with a carboxylic acid having a specified unsaturated group.

Thus, according to the present invention, there is provided a heparin derivative in which at least 0.5% of the entire hydroxyl groups of heparin are in the form of an ester represented by the following formula

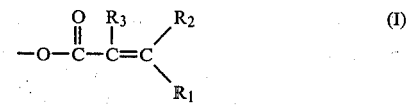

wherein $R_1$, $R_2$ and $R_3$ each represent a hydrogen atom, or an alkyl group having 1 to 6 carbon atoms.

The heparin derivative of this invention is a novel compound. First World Biomaterials Congress (Baden near Vienna, Austria, Apr. 8–12, 1980), Final Programme Book of Abstracts 1.3.6 describes the reaction of heparin with acrylic acid. Since this reaction is carried out in the presence of cerium IV, the reaction product is a compound in which heparin is bonded to acrylic acid through a carbon-carbon bond. Accordingly, this compound quite differs from the heparin derivative of this invention in which heparin is bonded to the carboxylic acid through an ester linkage.

The accompanying drawings show infrared absorption spectra of the novel heparin derivatives of this invention.

Figure 1:
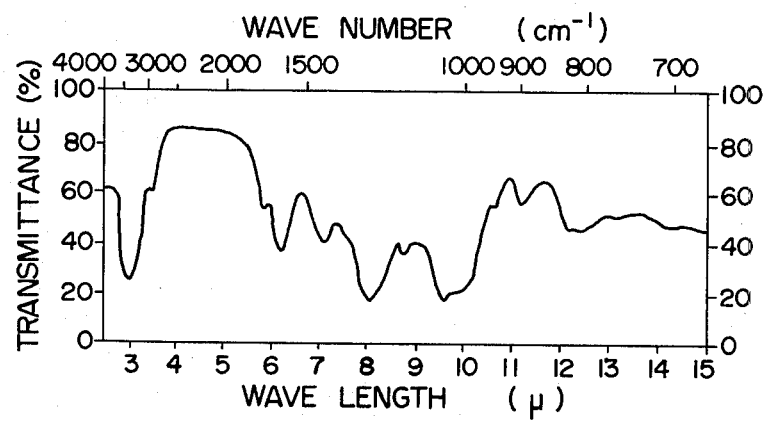
FIG. 1 is an infrared absorption spectrum of the heparin derivative obtained in Example 1.
Figure 2:
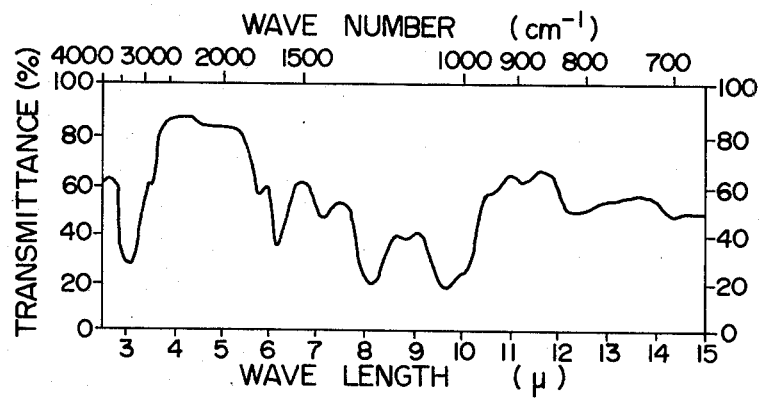
FIG. 2 is an infrared absorption spectrum of the heparin derivative obtained in Example 2.
Figure 3:
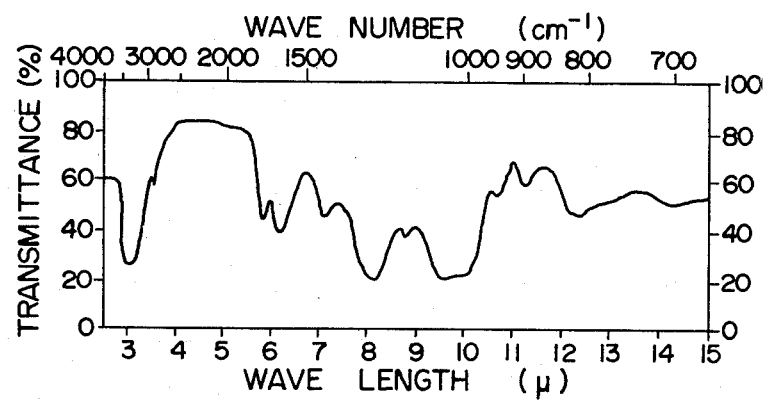
FIG. 3 is an infrared absorption spectrum of the heparin derivative obtained in Example 3.
Figure 4:
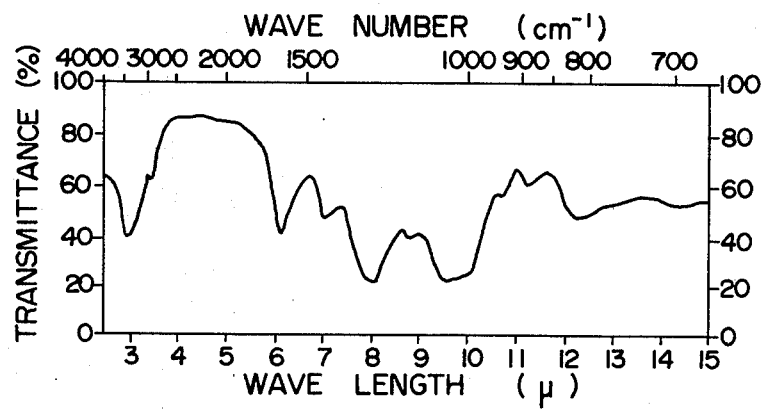
FIG. 4 is an infrared absorption spectrum of heparin used in synthesizing the heparin derivatives.

An absorption of an ester (—COO—), which is not seen in FIG. 4, appears at 1720 cm$^{-1}$ in FIGS. 1 to 3.

Heparin usually employed as an antithrombotic agent may be used as the starting heparin in the production of the novel heparin derivative of this invention. Heparin is usually extracted as a mucopolysaccharide from animal tissues, for example from hog intestine or whale intestine. It is commercially available as sodium heparin. It shows the activities described in Japanese Pharmacopoeia C-1235, or U.S. Pharmacopoeia XIX, p 229 (1975). Those which are therapeutically acceptable can be used in this invention.

As shown by formula (I), in the heparin derivative of this invention, an unsaturated group is introduced into the alcoholic hydroxyl moiety of heparin through an ester linkage. The site of introduction of the unsaturated group may be at any of the many alcoholic hydroxyl groups, and the number of such unsaturated groups is one or more. The ratio of introduction of ester linkages should be such that at least 0.5% of the entire hydroxyl groups of heparin are converted to the ester represented by formula (I).

The ratio of introduction, as used herein, is calculated as follows:

Heparin is usually a polymeric compound containing a disaccharide of the following structural formula

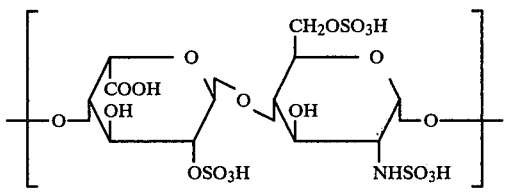

as one unit. (Not all of the units have three $SO_3H$ as in the above formula. Also, $SO_3H$ is sometimes present in the form of $SO_3Na$. But these facts are not relevant to the calculation of the ratio of introduction of ester groups.)

As the number of carbon atoms in one unit is 12, the molecular weight [H] of one unit of heparin is calculated as follows from the amount of carbon $[C_1]\%$ determined by elemental analysis.

$$[H] = 12.01 \times 12 \times 100/[C_1]$$

When ester groups are introduced, the ratio of introduction [D%] of the ester groups can be calculated from the following equation.

$$\frac{12.01 \times 12 + [N] \times 12.01 \times \frac{D}{100}}{[H] + \{[M] - 15\} \times \frac{D}{100}} \times 100 = [C_2]$$

wherein $[C_2]$ is the amount of carbon determined by elemental analysis of esterified heparin,

[M] is the amount of the ester represented by formula (I), and

[N] is the number of carbon atoms of the ester of formula (I).

As the ratio of introduction D% obtained corresponds to two hydroxyl groups, the ratio of introduction for one hydroxyl group is D/2. The D/2 value represents the ratio of introduction of ester linkages into the entire hydroxyl groups of heparin. A specific method of calculating this introduction ratio is shown in Example 1 to be given hereinbelow.

When an infrared absorption spectrum of the heparin derivative is taken by an infrared spectrophotometer (JASCO-A-102, a product of Nippon Bunko K.K.), an absorption of the ester is located at 1720 cm$^{-1}$ even when the ratio of introduction of ester groups is 1%. The maximum of the ratio of introduction of ester groups is 100%, but introduction of substantially 100% ester groups causes a great industrial loss. The ester introduction ratio may be not more than 80%, and at times, not more than 50%. Preferably, 1 to 80%, more preferably 3 to 50%, of the entire hydroxyl groups of heparin are converted to the ester represented by formula (I).

In formula (I), each of $R_1$, $R_2$ and $R_3$ represent a hydrogen atom or a lower alkyl group having 1 to 6 carbon atoms. These groups may be the same or different. Examples of the lower alkyl group are methyl, ethyl, propyl, isopropyl, butyl, isobutyl, heptyl and hexyl groups. Alkyl groups having 1 to 4 carbon atoms are preferred and a methyl group is especially preferred. Most preferably, both $R_1$ and $R_2$ are hydrogen atoms, and $R_3$ is a hydrogen atom or a methyl group.

The heparin derivative of this invention retains the inherent antithrombotic activity of heparin. Since an unsaturated group which is intrinsically irrelevant to the antithrombotic activity is introduced, the heparin derivative can be fixed to the desired site of a biomedical material by utilizing the activity of the unsaturated group. The heparin derivative exhibits superior antithrombotic activity even when it is in the fixed state.

The novel heparin derivative of this invention can be produced by a method which comprises reacting heparin with a halide or anhydride of an unsaturated carboxylic acid of the following formula

wherein $R_1$, $R_2$ and $R_3$ are as defined hereinabove, to esterify at least 0.5% of the entire hydroxyl groups of heparin.

In the unsaturated caboxylic acid of formula (II), $R_1$, $R_2$ and $R_3$ are most preferably such that $R_1$ and $R_2$ are hydrogen atoms, and $R_3$ is a hydrogen atom or a methyl group (i.e., acrylic or methacrylic acid). The halogen which constitutes the halide of the unsaturated carboxylic acid is preferably a chlorine or bromine atom, and the chlorine atom is especially preferred.

Examples of preferred halides or anhydrides of the unsaturated carboxylic acid include acryloyl chloride, methacryloyl chloride, acrylic anhydride and methacrylic anhydride. These compounds have high activity by themselves, and very readily react with the alcoholic hydroxyl groups of heparin to form the heparin derivative of formula (I). The site of an ester linkage in the heparin derivative may correspond to at least one of the many alcoholic hydroxyl groups of heparin. No particular limitation is imposed on the site and number of the ester linkages.

When the acid halide or acid anhydride is liquid in the reaction of heparin with the acid halide or anhydride of the unsaturated carboxylic acid, the reaction may be carried out in a homogeneous solution system or heterogeneous solution system after the addition of heparin. Preferably, the reaction is carried out in a homogeneous solution system using a solvent. The solvent that may be used is substantially non-reactive with the halide or anhydride of the unsaturated carboxylic acid of formula (II), and may, for example, be formamide, acetonitrile, chloroform, toluene, etc. Usually, these solvents have a weak power of dissolving heparin, and therefore, it is preferred to use heparin after subjecting it to a solubilizing treatment. Solubilization can be performed, for example, by converying heparin into its quaternary ammonium salt. A reagent for conversion to a quaternary ammonium salt may include, for example, cetyl pyridium chloride, cetyl trimethyl ammonium bromide, etc. Cetyl pyridium chloride is preferred.

The reaction of heparin (or a quaternary ammonium salt of heparin) with the acid halide or acid anhydride of the unsaturated carboxylic acid is conveniently carried out at not more than 100° C., preferably 0° to 70° C., more preferably at room temperature. Temperatures much higher than 100° C. are undesirable because they result in deactivation of heparin. The reaction time which depends upon the reaction temperature is usually about 5 seconds to about 50 hours.

In the esterification reaction using the acid halide and/or acid anhydride, known esterification catalysts may be used. For example, basic catalysts such as triethylamine or pyridine may be used. Other esterification catalysts may also be used. The reaction product is separated by re-precipitation, etc. and is sufficiently washed by repeating re-precipitation and washing. As a solvent for re-precipitation, acetone, chloroform, etc. are used preferably with a compound capable of removing the acid halide or anhydride of the unsaturated carboxylic acid by hydrolysis, such as water and ethanol.

In this manner, the heparin derivative of formula (I) having ester groups can be easily obtained.

The novel heparin derivative of this invention is useful for imparing antithrombotic activity to various biomedical materials having a surface to be in direct contact with the blood.

Examples of the biomedical material which is to be made antithrombotic by the novel heparin derivative of this invention include shaped articles such as catheters, blood bags, blood circuits, A-V shunts for artificial kidneys, dialysis membranes for artificial kidneys and tubes and pumping chambers for blood pumps. It is also possible to impart antithrombotic activity to precursors of these shaped articles, for example films or hollow articles.

The biomedical materials as shaped articles are composed of thermoplastic resins such as polyethylene, polypropylene, polyvinyl chloride, polyesters, polyamides, polycarbonates, polyurethanes, silicone resins and fluorocarbon resins; elastomers such as natural rubbers, synthetic rubbers, polyester ether elastomers and polyester ester elastomers; cellulose derivatives such as acetyl cellulose; and other resins.

Antithrombotic activity can be imparted to the biomedical material in the form of a shaped article by treating it with actinic light in the presence of the heparin derivative of this invention. The phrase "in the presence", as used herein, denotes the condition in which the surface of the shaped article is in contact with the heparin derivative, or the heparin derivative is impregnated in the surface layer portion of the shaped article. Preferably, this can be achieved by the following procedure. Specifically, the heparin derivative having an unsaturated group is dissolved to a concentration of about 0.001 to 100% by weight in a solvent capable of uniformly dissolving the heparin derivative, such as formamide, physiological saline or a mixture of water and ethanol, and the resulting uniform solution is kept in uniform contact with the blood-contacting surface of the shaped article. In this state, the surface of the shaped article is treated with actinic light. To keep the shaped article in uniform contact with the solution, a dipping method is preferably used by which the shaped article is dipped in the solution. In this actinic light treatment, the solvent may be used in combination with an organic solvent miscible uniformly with it, such as dimethyl formamide, dimethyl sulfoxide, acetonitrile, alcohols, and dioxane to increase the affinity of the solution with the shaped article. The concentration of the heparin derivative in the heparin solution is preferably 0.01 to 50% by weight, more preferably 0.05 to 10% by weight.

In the above actinic light treatment, an unsaturated monomer to be exemplfied hereinbelow may be added to the heparin solution in an amount of 1 to 10,000% by weight. The amount of the unsaturated monomer is preferably 10 to 5000% by weight, more preferably 50 to 1000% by weight, based on the weight of the heparin derivative. When the unsaturated monomer is to be used jointly, it is preferably added to a solution of the heparin derivative. The unsaturated monomer is preferably an ordinary vinyl compound, and specific examples include acrylic acid, methacrylic acid, methyl methacrylate, acrylonitrile, hydroxyethyl methacrylate, styrene, vinyl chloride, vinylpyridine, and N-vinylpyrrolidone. At least one of these unsaturated monomers may be used. Preferably, at least one of them is a hydrophilic unsaturated monomer. Preferred hydrophilic unsaturated monomers are, for example, acrylic acid, methacrylic acid, hydroxyethyl methacrylate and N-vinylpyrrolidone. The hydrophilic unsaturated monomer may be used in an amount 0.1 to 10 times the weight of the hydrophobic unsaturated monomer.

In accordance with this invention, a shaped article having a surface to be in contact with the blood is exposed to irradiation of actinic light in the presence of the heparin derivative having an unsaturated group by, for example, the following procedure (a) or (b).

(a) Ultraviolet light is irradiated at a temperature of $-10°$ C. to 70° C., preferably at room temperature, preferably in the presence of a photoreaction initiator.

(b) Electron beams and gamma-rays are irradiated under the following conditions.

The dose of irradiation is 0.001 Mrads to 100 Mrads, preferably 0.01 Mrad to 20 Mrads, more preferably 0.02 Mrad to 10 Mrads. Although the dose does not particularly affect the results, it is desirable that irradiation be performed uniformly on a shaped article to be treated. The irradiation temperature may be from $-10°$ C. to 70° C., and generally, it is advantageously room temperature.

The procedure (b) is especially preferred.

Many of the thermoplastic resin now used in biomedical materials are hydrophobic resins such as fluorocarbon resins. To bind the heparin derivative to a biomedical material composed of a hydrophobic polymer, it is preferred to hydrophilize the surface of the hydrophobic polymer prior to the treatment. Hydrophilization may be performed by any known method, such as grafting of a hydrophilic unsaturated monomer. For example, it can be conveniently performed by grafting a hydrophilic unsaturated monomer such as acrylic acid, methacrylic acid, hydroxyethyl methacrylate and vinylpyrrolidone by gamma-rays.

The biomedical materials to which antithrombotic activity has been imparted by the heparin derivative of this invention has much higher antithrombotic activity than conventional biomedical materials made from silicon rubbers, and has a reduced danger of bleeding owing to a large amount of heparin.

It has been found in accordance with this invention that the surface of a biomedical material can be rendered antithrombotic by performing the esterification reaction of this invention on the aforesaid surface. Specifically, antithrombotic activity can be conveniently imparted to the biomedical material by forming at least that surface of the material which comes into contact with the blood from a polymer having a carboxylic acid halide group and/or a carboxylic anhydride group in the side chain, and treating the resulting material with a heparin solution.

The polymer from which the blood-contacting surface of the biomedical material is made has a carboxylic halide group (—COX in which X is halogen) and/or a carboxylic anhydride group (—COOCO—) in the side chain of the molecule. Introduction of such groups into the side chain of a polymer can, for example, be performed by addition-polymerizing a halide or anhydride of a carboxylic acid having at least one carbon-carbon double bond in the molecule, or reacting it with another polymer. Examples of such a compound are the monohalides, dihalides and anhydrides of unsaturated carboxylic acids such as acrylic acid, methacrylic acid, maleic acid and cyclohexene-dicarboxylic acid. These compounds may be used either singly or as a mixture of two or more.

Examples of the polymer having a carboxylic acid halide group and/or a carboxylic anhydride group in the side chain include a polymer or copolymer obtained by addition-polymerization of the aforesaid compound; a copolymer obtained by addition-polymerization of the aforesaid compound with another monomer having a carbon-carbon double bond such as ethylene, propylene, vinyl chloride, styrene, acrylonitrile or butadiene; a graft copolymer obtained by graft copolymerizing the polymer of the aforesaid compound with the aforesaid monomer; a graft copolymer obtained by graft polymerizing a polymer of the aforesaid monomer with the aforesaid compound; a copolymer graft copolymer obtained by graft polymerization of the aforesaid compound with a known thermoplastic polymer or a flexible polymer such as a polyester, polyamide, polycarbonate, polyurethane, silicone resin, natural rubber or synthetic rubber; and mixtures of two or more of these.

Examples of the polyesters which form graft copolymers or matrix polymers by reaction with the carboxylic acid halide or carboxylic anhydride are polyethylene terephthalate, polytetraethylene terephthalate, polyethylene-2,6-naphthalate, polyhexamethylene terephthalate, and copolyesters of these polyesters with a minor proportion of at least one compound having an ester-forming group, such as adipic acid, dodecanedionic acid, trimellitic acid, isophthalic acid, phthalic acid, neopentyl glycol, hexamethylene glycol, pentaerythritol, polyethylene glycol or polytetramethylene glycol. Examples of the polyamide are polycaprolactam and polyhexamethylene adipate. Examples of the polycarbonate are aromatic polycarbonates derived from bisphenols such as bisphenol A, bisphenol Z and bisphenol S and phosgene or diphenyl carbonate. A dimethylsiloxane polymer is an example of the silicone resin. These polymers may be prepared by conventional known methods. In the present invention, all of the carboxylic acid halide groups or carboxylic anhydride groups in the side chain of the polymers should not be converted to carboxyl groups or other groups by hydrolysis before contact with the heparin solution. In the production of the polymers, therefore, it is preferred not to use a polymer or a reaction aid which has the function of converting the carboxylic acid halide group or the carboxylic anhydride group to a carboxyl group. Those polymers or reaction aids which convert only some of the carboxylic acid halide groups or carboxylic anhydride groups into carboxyl groups and do not substantially impair the objects of this invention may be used depending upon the ratio of conversion. For example, in the production of a polymer by suspension-polymerization or solution-polymerization, it is preferred to use a compound inert to the carboxylic acid halide group and/or the carboxylic anhydride group as a solvent. Furthermore, when a polymer swelling agent is used in the production of a graft copolymer or a matrix polymer, the swelling agent is preferably inert to the carboxylic acid halide group and the carboxylic anhydride groups.

The swelling agent may be selected from known organic solvents, and may be those which after a certain period of time from contact with the polymer at room temperature or at a suitable temperature, penetrate into the inside of the polymer at the contacting surface and cause changes in its volume, weight, shape, etc.

Specific examples of such solvents are acetonitrile, methylene chloride, tetrahydrofuran and dimethylnaphthalene for copolyesters; monochlorobenzene, methylene chloride and decalin for polyolefins; and methylene chloride and dioxane for polycarbonates.

These are only part of the examples, and suitable swelling agents may be selected depending upon the desired degree of swelling and the type and quality of the polymer.

The graft copolymer or matrix polymer having a carboxylic acid halide group and/or a carboxylic anhydride group in the side chain can be easily obtained by dipping a base polymer in a solution containing the desired proportions of a carboxylic acid halide or a carboxylic anhydride and the swelling agent for the polymer to swell the polymer and heating the polymer in the dipped state or after withdrawing from the solution, or irradiating actinic light on such a polymer. The solvent used at this time is preferably selected from those exemplified above as the swelling agent. Examples are monochlorobenzene for dissolving polyethylene under heat, and chloroform for dissolving polytetramethylene glycol copolybutylene terephthalate. The actinic light used at this time includes light energy in the broad sense such as ultraviolet light or microwaves, and ionizing radiations such as electron beams, gamma-rays, X-rays, and neutron rays. The ultraviolet light, electron beams and gamma-rays are especially preferred. At this time, it is preferred to include a polymerization promotor in the dipping solution. In the case of the heat reaction, a radical initiator such as benzyl peroxide and dicumyl peroxide is preferred as the polymerization promotor. In the case of ultraviolet irradiation, a sensitizer such as benzophenone and benzil ketal is preferred.

The shaped article whose surface in contact with the blood is formed of the polymer having a carboxylic acid halide group and/or a carboxylic anhydride group in the side chain can be easily obtained by shaping the aforesaid polymer in a manner in a conventional manner. Or it can be obtained by laminating the polymer to the surface of a shaped article by a melting method or a casting method. Or it can be obtained by shaping the base polymer in a conventional manner to form a shaped article, then reacting the surface of the resulting shaped article with a carboxylic acid halide or a carboxylic anhydride to change the surface to that of a graft copolymer or a matrix polymer. The last method is most preferred.

The shaped article to the surface of which is laminated a polymer having a carboxylic acid halide group and/or a carboxylic anhydride group in the side chain is produced from a thermoplastic resin such as polyethylene, polypropylene, polyesters, polyamides, polycarbonates, polyurethane or silicone resins, an elastomer such as natural rubber, synthetic rubbers, polyester ether elastomer, or polyester ester elastomer, and other resin.

Desirably, the polymer having carboxylic acid halide groups and/or carboxylic anhydride groups in the side chain has at least $10^{-9}$ equivalent/cm$^2$, preferably at least $10^{-8}$ equivalent/cm$^2$, especially preferably at least $10^{-7}$ equivalent/cm$^2$, of the aforesaid carboxylic acid halide groups and/or the carboxylic anhydride groups at that part or surface of the shaped article to which antithrombotic activity is to be imparted. The amount of these groups can be determined by known methods such as titration or back titration using a neutralization reaction, X-ray determination of the amount of metal by metal salt exchange, etc.

The resulting shaped article is then contacted with the heparin solution. At this time, all of the carboxylic acid halide groups or carboxylic anhydride groups should not be changed to carboxyl groups by hydrolysis, etc.

The heparin solution used in this invention is a solution of heparin in an organic solvent. The organic solvent may be an ordinary organic solvent which does not have the property of changing all of the carboxylic acid halide groups or carboxylic anhydride groups into carboxyl groups by hydrolysis, etc. Examples are methylene chloride, formamide, and a mixture of dimethyl sulfoxide and chloroform.

Commercially available heparin (sodium salt) is dissolved in the organic solvent to prepare the heparin solution. When heparin is insoluble or sparingly soluble, it is necessary to subject it to a solubilizing treatment. Solubilization can easily be achieved by converting heparin into its quaternary ammonium salt. A reagent for conversion to the quaternary ammonium salt may, for example, be cetyl pyridium chloride and cetyl trimethyl ammonium bromide. Cetyl pyridium chloride is preferred. The concentration of heparin, for example solubilized heparin, is not more than about 10% by weight, preferably 1 to 5% by weight.

Treatment with the heparin solution is carried out by contacting the shaped article with the solution. The contacting time is at least 10 seconds, preferably 30 seconds to 30 hours, especially preferably 1 minute to 5 hours. The temperature at which the contacting is carried out is not more than 100° C., preferably not more than 50° C., especially preferably at room temperature. Desirably, the treating time and temperature are selected depending upon the relation of the swellability of the polymer forming the surface to be treated to the solvent in the heparin solution. At the time of the treatment, a known esterification catalyst may be used such as a basic catalyst (e.g., triethylamine or pyridine).

The biomedical material can be rendered antithrombotic by the heparin derivative of this invention by binding heparin to that surface of the shaped article of the polymer having the specified groups which makes direct contact with the blood. The resulting antithrombotic biomedical material has much higher antithrombotic activity than those made from silicone rubbers which have been previously used for medical treatment, and has a reduced danger of bleeding owing to a large amount of heparin.

The following Examples illustrate the present invention in greater details. In these examples, all parts and percentages are by weight unless otherwise indicated.

Heparin used in the Examples was a product of Eastman Kodak Co. Other reagents were either those specified in Japanese Pharmacopoeia, or class 1 reagents.

The rabbit blood used in the antithrombosis test was prepared by mixing the blood taken from the vein of the rabbit ear with a 3.8% aqueous solution of sodium citrate in a volume ratio of 9:1, maintaining the resulting mixture at 37° C. for 1 minute, and then mixing it with the same volume of a 1/40 M aqueous solution of calcium chloride.

EXAMPLE 1

Heparin (5 parts) and 1.5 parts of acrylic anhydride were dissolved in 100 parts of formamide, and reacted at room temperature for 48 hours with stirring. Acetone (1000 parts) was added to the reaction mixture to form a precipitate. The precipitate was separated by filtration, and re-dissolved in 40 parts of water. Then, the solution was subjected to re-precipitation using 1000 parts of ethanol. The precipitate was subjected to two cycles of re-precipitation and washing with water-ethanol, and the product was dried in vacuo at 25° C. to obtain 4 parts of a white solid.

The infrared adsorption spectrum of the white solid is shown in FIG. 1. This spectrum was substantially the same as that of the starting heparin except that a new absorption of the ester linkage was seen at 1720 cm$^{-1}$.

The white solid turned brown at 240° to 250° C. as does the starting heparin. The elemental analysis values for the white solid were 21.23% C., 3.74% H and 1.85% N, while those of the starting heparin were 20.42% C, 3.58% H and 1.88% N. The infrared absorption spectrum of the starting heparin is shown in FIG. 4.

By the following calculation from the above elemental analysis values, it was found that about 8.5%, based on the hydroxyl groups of heparin, of acrylic acid was introduced through an ester linkage.

Heparin is a polymeric compound having a disaccharide of the following structural formula

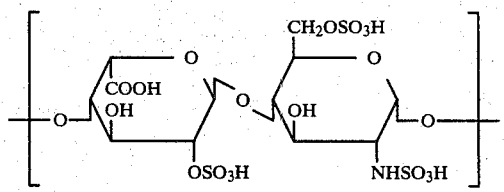

as one unit. (Not all of the units have three SO$_3$H as in the above formula, but this is irrelevant to the calculation of the ratio of introduction of acrylic acid.)

Since the number of carbon atoms in one unit is 12, the molecular weight (H) of one unit of heparin is calculated as follows from the amount (20.42%) of carbon determined by elemental analysis.

$$\frac{12.01 \times 12}{(H)} \times 100 = 20.42$$

$$\therefore (H) = 705.8$$

When methacrylic acid is introduced through an ester linkage, the structural formula of the unit changes to the following.

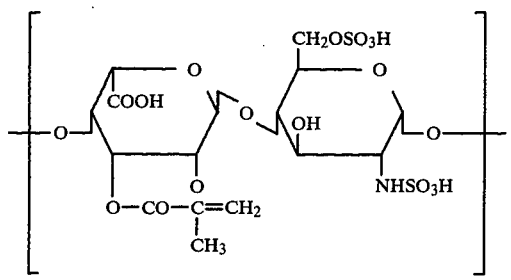

As a result of esterification, 4 carbon atoms increased for each unit, and the increase of the molecular weight was 68.08.

Hence, the ratio of introduction (D%) of methacrylic acid per two hydroxyl groups (i.e. per unit) is calculated as follows from the amount (21.23%) of carbon determined by elemental analysis of the heparin ester.

$$\frac{12.01 \times 12 + 4 \times 12.01 \times \frac{D}{100}}{705.8 + 68.08 \times \frac{D}{100}} \times 100 = 21.23$$

$$\therefore D = 17.0(\%)$$

Hence, the ratio of introduction per hydroxyl group is 17.0/2=8.5(%).

The resulting white solid was added in each of the amounts shown in Table 1 to the rabbit blood, and gently held at 37° C. in a glass test tube. The time which elapsed until a thrombus formed was measured. The results are shown in Table 1.

For comparison, the thrombus formation test was conducted using heparin instead of the heparin derivative. The results are also shown in Table 1.

TABLE 1

| Antithrombotic agent | Amount added (mg/ml) | Time elapsed until the formation of a thrombus (minutes) |
|---|---|---|
| Heparin derivative obtained in Example 1 | 0.001 | 7 |
|  | 0.01 | 21 |
| Untreated heparin | 0.001 | 9 |
|  | 0.01 | 19 |

It is seen from the results obtained that the antithrombotic activity of the heparin derivative having acrylic acid introduced thereinto was equivalent to that of heparin.

EXAMPLE 2

Ten parts of cetyl pyridium salt of heparin was dissolved in a mixture of 70 parts of dimethyl sulfoxide and 30 parts of chloroform, and 10 parts of methacrylic anhydride was added. The mixture was reacted at 40° C. for 3 hours. The reaction product was re-precipitated once with chloroform-ethyl ether and twice with water-ethanol, and then treated with a 2.1 M aqueous solution of sodium chloride. Sodium chloride was removed by using a cellophane membrane in a customary manner, and the residue was reprecipitated with water-ethanol and washed to separate 3 parts of a white solid as a purified product.

In the same way as in Example 1, 0.01 mg/ml of the white solid was added to the rabbit blood, and its antithrombotic activity was observed. The time which elapsed until a thrombus was seen to form was 20 minutes. The infrared absorption spectrum of the white solid is shown in FIG. 2. The spectrum showed an absorption of the ester group at 1720 cm$^{-1}$ which was not present in the heparin before the reaction. Furthermore, the white solid turned brown at 240° to 250° C. The elemental analysis values of the white solid were 22.01% C, 3.62% H and 1.91% N, and the amount of methacrylic acid introduced was 13% based on the hydroxyl groups.

EXAMPLE 3

Heparin (1.5 parts) and 0.5 part of methacryloyl chloride were added to 25 parts of formamide, and 0.5 part of pyridine was added. The mixture was reacted at room temperature for 0.5 hour.

The reaction product was re-precipitated with water-cooled ethanol, and again dissolved in water. It was again precipitated with a mixture of ethanol and chloroform (60:40 by volume) to separate a white solid as a purified product.

The infrared absorption spectrum of the resulting white solid is shown in FIG. 3. The spectrum showed an absorption of the ester linkage at 1720 cm$^{-1}$. The white solid turned brown at 240° to 250° C. The elemental analysis values of the white solid were 23.07% C, 3.64% H and 1.92% N, and 21% of the hydroxyl groups of heparin were esterified with methacrylic acid.

EXAMPLE 4

Example 3 was repeated except that the amount of the methacryloyl chloride was changed to 0.05 part, and the amount of pyridine was changed to 0.05 part.

The resulting white solid was found to be methacrylic acid-introduced heparin having a ratio of introduction of ester groups of 1.2% calculated from the amount of carbon (20.53%) determined by elemental analysis. In the infrared absorption spectrum of the white solid, a shoulder ascribable to the ester was noted at 1720 cm$^{-1}$.

EXAMPLE 5

Example 3 was repeated except that the amount of the methacryloyl chloride was changed to 1.5 parts, and the amount of the pyridine was changed to 1.5 parts, and the reaction temperature was changed to 50° C.

The resulting white solid was found to be methacrylic acid-introduced heparin having a ratio of introduction of ester groups of 54% calculated from the amount of carbon (25.15%) determined by elemental analysis. In the infrared absorption spectrum of the white solid, a sharp absorption ascribable to the ester groups was seen at 1720 cm$^{-1}$.

EXAMPLE 6

Polytetramethylene terephthalate (reduced specific viscosity 2.31 dl/g) having copolymerized therewith 60% of polytetramethylene glycol having a molecular wtight of 2000 was made into chips. The chips were passed through an extruder at 250° C., and extruded from a slit having a width of 0.5 mm fitted to its tip to make a sheet having a thickness of 0.5 mm.

One piece of the sheet was cut out, put into a petri dish and was impregnated entirely with a solution prepared by mixing 100 parts of acetonitrile with 1 part of acrylic acid and 1 part of cetyl pyridium salt of heparin derivative obtained by treating the heparin derivative with an aqueous solution of cetyl pyridium chloride.

Gamma-rays were irradiated in a dose of 0.1 Mrad onto the petri dish containing the sheet sample. Then, the sheet was taken out, washed with acetonitrile, fully washed successively with a 50% aqueous solution of methylene chloride and ethanol, a 2.1 M aqueous solution of sodium chloride, and pure water, and dried.

The resulting sheet was dipped in an aqueous solution of toluidine blue to test the color formation of heparin. The sheet formed a reddish violet color, and thus, the presence of heparin was ascertained.

EXAMPLE 7

Ten parts of cetyl pyridium salt of heparing was dissolved in a mixture of 70 parts of dimethyl sulfoxide and 30 parts of chloroform, and 10 parts of acrylic anhydride was added. The mixture was reacted at 40° C. for 3 hours. The resulting product was re-precipitated once with chloroform-ethyl ether and twice with water-ethanol and then treated with a 2.1 N aqueous solution of sodium chloride. Then, in a customary manner, sodium chloride was removed by using a cellophane membrane. The residue was further re-precipitated with water-ethanol and washed. The resulting solid white solid turned brown at 240° to 250° C., and from the elemental analysis values, the amount of acrylic acid introduced was found to be 13% based on the hydroxyl groups of heparin.

The cetyl pyridium salt of heparin used was obtained by reacting heparin (a product of Eastman Kodak Co., conforming to the standards of U.S. Pharmacopoeia) with cetyl pyridium chloride in a customary manner.

Ten parts of a polyester ester block copolymer (having a reduced specific viscosity of 1.53 dl/g measured at 35° C. in ortho-chlorophenol in a concentration of 1.2 g/dl) obtained by copolymerizing 67% of polycaprolactone, 10% of polyethylene terephthalate and 23% of polybutylene terephthalate was dissolved in 100 parts of chloroform. The solution was coated on a glass test tube having an inside diameter of about 1 cm and a length of about 10 cm, and dried. Then, the test tube was filled with a solution prepared by dissolving 1 part of the heparin esterified with acrylic acid in 100 parts of water-ethanol (50:50 by weight), and gamma-rays were irradiated in a dose of 0.1 Mrad onto the test tube. The test tube was fully washed with water-ethanol (50 parts-50 parts), physiological saline and water, and air-dried at room temperature.

An aqueous solution of toluidine blue was put into the test tube. A color of reddish violet formed, and the presence of heparin was ascertained.

The blood taken from a rabbit was put into the test tube not subjected to the color formation test, and hemolysis and thrombosis were examined. The results are shown in Table 2.

TABLE 2

| | | Time of contact with the blood | | |
|---|---|---|---|---|
| | Test items | 20 min. | 1 hour | 3 hours |
| Example 7 | Hemolysis | No | No | No |
| | Thrombosis | No | No | No |
| Comparative | Hemolysis | No | — | — |
| Example 1 | Thrombosis | Yes | — | — |

In Table 2, Comparative Example 1 refers to the case of coating a siliconize surface treating agent (a product of Fuji Systems Co., Ltd.) on the glass test tube.

EXAMPLES 8 TO 10 AND COMPARATIVE EXAMPLES 2 TO 4

Heparin (15 parts) and 0.5 part of methacryloyl chloride were added to 25 parts of formaldehyde, and 0.5 part of pyridine was further added. The mixture was reacted at room temperature for 0.5 hour. Then, the reaction product was re-precipitated with ice-cooled ethanol, and again dissolved in water. The mixture of ethanol and chloroform (volume ratio 60:40) to separate a white solid as a pure product. The white solid turned brown at 240° to 250° C. Elemental analysis led to the determination that the white solid resulted from esterification of 21% of the hydroxyl groups of heparin with methacrylic acid.

Five parts of a polyester polyether block copolymer having a reduced specific viscosity (measured at 35° C. in ortho-chlorophenol in a concentration of 1.2 g/dl) of 2.31 g/dl and having copolymerized therewith 60% of polytetramethylene glycol having a molecular weight of 2000 was dissolved in 100 parts of chloroform. The solution was coated on a glass test tube having an inside diameter of about 1 cm and a length of about 10 cm, and dried. The test tube was then filled with a solution obtained by dissolving 0.67 part of methacrylic acid-introduced heparin in 100 parts of a mixture of physiological saline and ethanol in a volume ratio of 70:30, and adding acrylic acid to the solution in the amounts indicated in Table 3. Gamma-rays were irradiated on the test tube at a dose of 0.1 Mrad. The test tube was thoroughly washed with physiological saline and then with water, and dried in the air at room temperature.

When an aqueous solution of toluidine blue was put into the test tube, a color of reddish violet formed. Hence, the presence of heparin was ascertained.

The same blood test as in Example 7 was performed, amnd the results are shown in Table 3.

TABLE 3

| Example (Ex.) or Comparative Example (CEx.) | Amount of acrylic acid (parts) | Test items | Time of contact with the blood | | |
|---|---|---|---|---|---|
| | | | 20 min. | 1 hour | 2 hours | 3 hours |
| Ex. 8 | 0 | Hemolysis | No | Yes | — | — |
| | | Thrombosis | No | Yes | — | — |
| Ex. 9 | 0.67 | Hemolysis | No | No | No | — |
| | | Thrombosis | No | No | Yes | — |
| Ex. 10 | 3.30 | Hemolysis | No | No | No | No |
| | | Thrombosis | No | No | No | Yes |
| CEx. 2 | 0 | Hemolysis | No | — | — | — |
| | | Thrombosis | Yes | — | — | — |
| CEx. 3 | 0 | Hemolysis | No | No | — | — |
| | | Thrombosis | No | Yes | — | — |
| CEx. 4 | 0 | Hemolysis | No | No | — | — |
| | | Thrombosis | No | Yes | — | — |

Comparative Example 2 refers to the case of coating the glass tube with a siliconize surface treating agent (a product of Fuji Systems Co., Ltd.). In Comparative Example 3, 0.01 mg/ml of heparin was added to the rabbit blood. in Comparative Example 4, the aforesaid methacrylic acid-introduced heparin was added.

EXAMPLES 11 TO 13 AND COMPARATIVE EXAMPLES 5 TO 7

Heparin (1.5 parts), 0.1 part of methacryloyl chloride and 0.1 part of pyridine were added to 25 parts of formamide, and reacted at room temperature for 0.5 hour. The reaction mixture was worked up in the same way as in Example 8 to obtain heparin having 7% of methacrylic acid introduced thereinto based on the hydroxyl groups of heparin.

Acetyl cellulose (10 parts) was dissolved in 100 parts of acetone, and the solution was coated on a glass test tube having an inside diameter of 1 cm and a length of about 10 cm and dried. Acrylic acid was added in the amounts indicated in Table 4 to a solution of 0.67 part of the resulting heparin derivative in 100 parts of physiological saline. The resulting solution was filled into the coated test tube. Gamma-rays were irradiated onto the test tube at a dose of 0.1 Mrad. The test tube was washed with physiological saline and then with water, and air-dried at room temperature. The presence of heparin in the test tube was determined by color formation using an aqueous solution of toluidine blue.

Using the resulting test tube, the same blood test as in Example 7 was performed, and the results are shown in Table 4.

TABLE 4

| Example (Ex.) or Comparative Example (CEx.) | Amount of acrylic acid (parts) | Test items | Time of contact with the blood | | |
|---|---|---|---|---|---|
| | | | 20 min. | 1 hour | 2 hours |
| Ex. 11 | 0 | Hemolysis | No | — | — |
| | | Thrombosis | Yes | — | — |
| Ex. 12 | 0.67 | Hemolysis | No | No | No |
| | | Thrombosis | No | No | Yes |
| Ex. 13 | 3.30 | Hemolysis | No | No | No |
| | | Thrombosis | No | No | No |
| CEx. 5 | 0 | Hemolysis | No | — | — |
| | | Thrombosis | Yes | — | — |
| CEx. 6 | 0 | Hemolysis | No | No | — |
| | | Thrombosis | No | Yes | — |
| CEx. 7 | 0 | Hemolysis | No | No | — |
| | | Thrombosis | No | Yes | — |

In Comparative Example 5, the glass test tube was coated with a siliconize surface treating agent (a product of Fuji Systems Co., Ltd.). In Comparative Example 6, heparin was added to the rabbit blood at a rate of 0.01 mg/ml. In Comparative Example 7, the methacrylic acid-introduced heparin was added at a rate of 0.01 mg/ml.

EXAMPLE 14

A cannula made of Teflon (trademark) was dipped in fully deaerated acrylic acid. The system was sealed up with nitrogen, and gamma-rays were irradiated at room temperature from Co 60 for 1 hour at a dose of 0.1 Mrad/hr. After the irradiation, the cannula was fully washed and dried. The ratio of grafting was 2%. The ratio of grafting was calculated from the following equation.

$$\text{Ratio of grafting (\%)} = \frac{\left[\begin{array}{c}\text{Dry weight}\\\text{after the}\\\text{grafting}\\\text{treatment}\end{array}\right] - \left[\begin{array}{c}\text{Dry weight}\\\text{after the}\\\text{grafting}\\\text{treatment}\end{array}\right]}{\left[\begin{array}{c}\text{Dry weight after the}\\\text{grafting treatment}\end{array}\right]} \times 100$$

The graft-treated cannula was dipped in a solution prepared by dissolving 2 parts of the same methylacrylic acid-introduced heparin as in Example 8 in a mixture of water and methanol (70:30 by volume) and adding 5 parts of acrylic acid. The system was sealed up with nitrogen, and gamma-rays were again irradiated at room temperature at a dose of 0.1 Mrad. The treated cannula was fully washed, and dipped in an aqueous solution of toluidine blue. A color of reddish violet formed, and thus, the presence of heparin was ascertained.

EXAMPLE 15

A polyester ether block copolymer (reduced specific viscosity 2.90 dl/g; measured at 35° C. in orthochlorophenol in a concentration of 1.2 g/dl) was prepared from 33 parts of a hard segment obtained by the reaction of a mixture of ethylene glycol and tetramethylene glycol (33:67 by mole) with dimethyl terephthalate and 67 parts of a soft segment derived from polytetramethylene glycol having a molecular weight of 2000. Chips of the copolymer were extruded through a tube die under ice cooling to obtain a transport tube having an inside diameter of 3 mm and an outside diameter of 5 mm.

The tube was cut to a length of 25 cm and both ends were tapered. The tapered tube was dipped in a solution prepared by dissolving 2 parts of the same methacrylic acid-introduced heparin in a mixture of physiological saline and methanol (70:30 by volume) and adding 5 parts of acrylic acid. The system was sealed up with nitrogen, and gamma-rays were irradiated at room temperature for 1 hour at a dose of 0.1 Mrad/hr. After the irradiation, the tube was fully washed, and dried.

The treated tube was connected to the carotid vein of an adult dog through the carotid artery, and embedded in the skin. It was subjected to a long-term antithrombosis test. No thrombus formation was noted for a period of more than 40 days, and the tube showed excellent antithrombotic activity.

EXAMPLES 16 AND 17 AND COMPARATIVE EXAMPLES 8 AND 9

Five parts of a polyester polyether block copolymer having a reduced specific viscosity, measured at 35° C. in ortho-chlorophenol in a concentration of 1.2 g/dl, of 2.31 dl/g and composed of polytetramethylene terephthalate having copolymerized therewith 60% of polytetramethylene glycol having a molecular weight of 2000 was dissolved in 100 parts of chloroform. The solution was coated on a glass test tube having an inside diameter of about 1 cm and a length of about 10 cm.

The test tube was then filled with a solution of acrylic anhydride in the amounts indicated in Table 5 in 100 parts of acetonitrile. Gamma-rays were irradiated onto the test tube at a dose of 0.1 Mrad. The test tube was fully washed with acetonitrile and then dried to form a composite polymer-coated test tube.

Separately, heparin purschased from Eastman Kodak Co. (conforming to the standards of U.S. Pharmacopoeia) was dissolved in a 0.04 mole aqueous solution of NaCl, and cetyl pyridium chloride was added to precipitate a cetyl pyridium salt of heparin. The heparin salt was separated by filtration, washed and dried. The product (2 parts) was dissolved in 100 parts of methylene chloride. The heparin solution obtained was filled into the composite polymer-coated test tube, and allowed to stand for 1 minute. Then, the test tube was successively washed with a 50% aqueous solution of ethanol, a 2.1 M aqueous solution of NaCl and pure water, and then dried.

When an aqueous solution of toluidine blue was put into the test tube, a color of reddish violet formed. Hence, the presence of heparin was ascertained.

The rabbit blood was put into the test tube not subjected to the color formation test, and observed at 37° C. for hemolysis and thrombosis. The results are shown in Table 5.

TABLE 5

| Example (Ex.) or Comparative Example (CEx.) | Amount of acrylic anhydride (parts) | Test items | Time of contact with the blood | | |
|---|---|---|---|---|---|
| | | | 10 min. | 1 hour | 3 hours |
| Ex. 16 | 1 | Hemolysis | No | No | No |
| | | Thrombosis | No | No | No |
| Ex. 17 | 10 | Hemolysis | No | No | No |
| | | Thrombosis | No | No | No |
| CEx. 8 | 0 | Hemolysis | No | Yes | — |
| | | Thrombosis | No | Yes | — |
| CEx. 9 | 0 | Hemolysis | No | — | — |
| | | Thrombosis | Yes | — | — |

In Comparative Example 8, the rabbit blood was added to heparin at a rate of 0.002 mg/ml. In Comparative Example 9, a siliconize surface treating agent (a product of Fuji Systems Co., Ltd.) was coated on the test tube.

EXAMPLE 18

A solution of 50 parts of acrylic anhydride in acetonitrile was subjected to irradiation of gamma-rays at a dose of 0.1 Mrad. The reaction product was separated by filtration, and dried. The resulting polymeric compound was a white non-tacky solid.

Five parts of a cetyl pyridium salt of heparin was dissolved in a mixture consisting of 70 parts of dimethyl sulfoxide and 30 parts of chloroform, and 5 parts of the polymeric compound was added. The resulting heterogenous solution was stirred to form a solution of the heparin derivative.

The solution was coated on a glass test tube in the same way as in Example 16, washed, and dried. Using the coated test tube, the rabbit blood was tested. As a result, even after a lapse of 3 hours, the blood showed no hemolysis nor thrombosis.

EXAMPLE 19

Polyethylene terephthalate having copolymerized therewith 70% of caprolactone was melted and molded into a tube having an inside diameter of 5 mm and an outside diameter of 8 mm. One end of the tube was then sealed.

The tube was filled with a solution of 5 parts of acryloyl chloride in 95 parts of toluene, and gamma-rays were irradiated thereon at a dose of 0.1 Mrad. Using the resulting tube, the same blood test as in Example 16 was performed. After standing for 3 hours, the blood showed no hemolysis nor thrombosis.

What we claim is:

1. A method for imparting antithrombotic activity to a biomedical material, which comprises treating that surface of the biomedical material which makes contact with the blood with actinic light in the presence of a heparin derivative in which at least 0.5% of the entire hydroxyl groups of heparin are in the form of an ester of the following formula

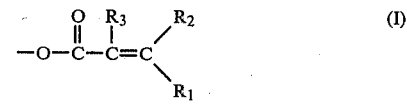

wherein $R_1$, $R_2$ and $R_3$ each represent a hydrogen atom or an alkyl group having 1 to 6 carbon atoms.

2. The method of claim 1 wherein at least the surface of said biomedical material is a hydrophilic substance.

3. A method for imparting antithrombotic activity to a biomedical material, which comprises forming at least that surface of the biomedical material which makes contact with the blood from a polymer having a carboxylic acid halide group and/or a carboxylic anhydride group in the side chain, and treating said surface with a solution of heparin wherein at least 0.5% of the entire hydroxyl groups of heparin are esterified.

4. The method of claim 1 wherein both $R_1$ and $R_2$ are hydrogen atoms and $R_3$ is a hydrogen atom or a methyl group.

5. The method of claim 1 wherein the treatment with actinic light is conducted at a temperature of from −10° C. to 70° C.

* * * * *